(12) United States Patent
Nielsen et al.

(10) Patent No.: US 6,242,574 B1
(45) Date of Patent: Jun. 5, 2001

(54) ANTIMICROBIAL PROTEINS

(75) Inventors: Klaus Kristian Nielsen, Copenhagen; Anne Kroll Kristensen, Birkerod; Janne Brunstedt, Roskilde, all of (DK)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 09/091,590

(22) PCT Filed: Dec. 20, 1996

(86) PCT No.: PCT/EP96/05765

§ 371 Date: May 6, 1999

§ 102(e) Date: May 6, 1999

(87) PCT Pub. No.: WO97/23617

PCT Pub. Date: Jul. 3, 1997

(30) Foreign Application Priority Data

Dec. 21, 1995  (GB) ................................ 9526238

(51) Int. Cl.[7] ............................ A01H 1/00; C07H 21/04; C07K 14/415; C12N 5/14
(52) U.S. Cl. .................. 530/370; 435/69.1; 435/70.1; 435/71.1; 435/71.2; 435/410; 435/418; 435/419; 530/300; 530/324; 530/379; 530/370; 536/23.6; 800/279; 424/195.1
(58) Field of Search ................... 435/69.1, 70.1, 435/71.1, 71.2, 410, 418, 419; 530/300, 324, 370, 379; 536/23.6; 800/279; 424/195.1

(56) References Cited

FOREIGN PATENT DOCUMENTS

| 0 612 847 | 8/1994 | (EP) . |
| WO9217591 | 10/1992 | (WO) . |
| WO9220801 | 11/1992 | (WO) . |
| WO9504754 | 2/1995 | (WO) . |
| WO9511306 | 4/1995 | (WO) . |

OTHER PUBLICATIONS

Kanazin et al. PNAS USA, vol. 93, p. 11746–11750 Oct. 1996.*
Dieryck, W. et al., Plant Molecular Biology, 19, 707–709 (1992).
Jakobsen, K. et al., Plant Molecular Biology, 12, 285–293 (1989).
Ye, Z–H. et al., Plant Physiology, 103, 805–813 (1993).
Raynal, M. et al., EMBL Sequence Database, REL 37, Accession No. Z27019 (Nov. 1993).
Pyee, J. et al., EMBL Sequence Database, REL. 39, Accession No. L29767 (Mar. 1994).
Martine–Rousseau–Limouzin and Bernard Fritig, Plant Physiol. Biochem., 29(2), 105–117 (1991).
Nielsen, K. K., et al., "Extracellular antifungal proteins in sugar beet leaves", Keystone Symposium On Host–Fungus Pathogenic Interaction, Taos, New Mexico USA, Feb. 25–Mar. 3, 1995, Journal of Cellular Biochemistry supplement (19B), 158, XP00209153 (See.

* cited by examiner

Primary Examiner—Phuong T. Bui
(74) Attorney, Agent, or Firm—J. Timothy Meigs

(57) ABSTRACT

Isolated proteins having anti-fungal activity against at least Cercospora spp. The proteins contain an amino acid sequence which has at least 95% sequence identity to any of the following sequences: SEQ ID NO:3 wherein the amino acid in position 80 is alanine instead of valine, SEQ ID NO:5 and SEQ ID NO:6. Recombinant DNA molecules encoding such proteins. A vector comprising such DNA which is expressible in plants and which is linked to a plant operable promoter and terminator. Plants transformed with such recombinant DNA; the progeny of such plants which contain the DNA stably incorporated and hereditable in a Mendelian manner, and/or the seeds of such plants or such progeny.

11 Claims, 6 Drawing Sheets

SEQUENCE LISTING

<160> NUMBER OF SEQ ID NOS: 35

<210> SEQ ID NO 1
<211> LENGTH: 722
<212> TYPE: DNA
<213> ORGANISM: Beta vulgaris

<400> SEQUENCE: 1

```
accatctagt accaattaat tacaactatc tctctctctc tttctctcta ggcctctttc      60
ttaaagtttg tgataggatt agcagcaatc ccaacatggc tagggcagct aatctaaagc     120
tgttatgcgc atttattctg agcatagtgg tgttcacacc acatgcagag gccgccatta     180
actgtggtct ggtctctcag agccttgcag catgccttgg attcctagag aatggtcagg     240
gaccaaatgc agcttgctgc aacggtgtta agacactccg aaacttgact cccacaaccc     300
aggacaaaag aacggcttgt aggtgcatga aatcagccgc ttcagccatt cccggcatca     360
accataagta ctcagctgca cttcccggca aatgtggggt cagcattcca gggcctgttg     420
gcccccaggc agactgctct cagatccact agacctgaag tttccaggag gggaacacta     480
gcaaaacaaa gaatagttgg gttctgactt catacaagca aaatctatag taaattccca     540
tgaagtgcat gctttctgga actttctgct tatcaagtta ttattacata tataccatgt     600
gtgcttctta catctaaagt gacttacata atctccaatt ccatgtaaga gatagcaagg     660
aagattaaat attgaaataa aatcycttat tggttaaahc ccaaaaaaaa aaaaaaaaa      720
```

```
                                                                            aa                                                                    722

<210> SEQ ID NO 2
<211> LENGTH: 587
<212> TYPE: DNA
<213> ORGANISM: Beta vulgaris
<220> FEATURE:
<221> NAME/KEY: CDS
<222> LOCATION: (129)..(374)

<400> SEQUENCE: 2
ataagtggca agcaaaaaga aatcatttca ctaaaaactg caaaaagaaa atggagaagt          60
catcatgctt taagctggtt ttcttagtct ttctgttgct caacatttca gcttcaacac        120 ttgcaaga atg caa cca act ata atg gaa gaa ctt aca aag gaa caa gtt         170
         Met Gln Pro Thr Ile Met Glu Glu Leu Thr Lys Glu Gln Val
         1               5                  10 ctt gaa gaa ctt ggt gct tac aag cag ata ata gca tca gca gca aca           218
Leu Glu Glu Leu Gly Ala Tyr Lys Gln Ile Ile Ala Ser Ala Ala Thr
15                  20                  25                  30 aga gac cgc ggc gag tta tta aga acg gtg ata gaa gcg gtt gcg cga           266
Arg Asp Arg Gly Glu Leu Leu Arg Thr Val Ile Glu Ala Val Ala Arg
                35                  40                  45 ccg cga ccg cga ccg tgc ata agg gct ggc ggc tac tgt aac att ttg           314
Pro Arg Pro Arg Pro Cys Ile Arg Ala Gly Gly Tyr Cys Asn Ile Leu
        50                  55                  60 aac gta tgt tgt gct ggg ttg act tgt gag gaa cat gat ata caa gac           362
Asn Val Cys Cys Ala Gly Leu Thr Cys Glu Glu His Asp Ile Gln Asp
65                  70                  75 gcc gtc tgc gtc taaatcttgg acttgcttaa aaaaatgtgt tattataagt              414
Ala Val Cys Val
        80 gtatttggcc ttttaggctt gatcttcaat ttcgtcttta agcttagtca tctaactagc        474 gtgtctgttt gtcaataaag atcattgtct tctctagaca attatggact tcttgatgct        534 tttattttaa taatataaaa tatttcctcg ctttcaaaaa aaaaaaaaaa aaa              587

<210> SEQ ID NO 3
<211> LENGTH: 82
<212> TYPE: PRT
<213> ORGANISM: Beta vulgaris

<400> SEQUENCE: 3

Met Gln Pro Thr Ile Met Glu Glu Leu Thr Lys Glu Gln Val Leu Glu
1               5                  10                  15

Glu Leu Gly Ala Tyr Lys Gln Ile Ile Ala Ser Ala Ala Thr Arg Asp
            20                  25                  30

Arg Gly Glu Leu Leu Arg Thr Val Ile Glu Ala Val Ala Arg Pro Arg
        35                  40                  45

Pro Arg Pro Cys Ile Arg Ala Gly Gly Tyr Cys Asn Ile Leu Asn Val
    50                  55                  60

Cys Cys Ala Gly Leu Thr Cys Glu Glu His Asp Ile Gln Asp Ala Val
65                  70                  75                  80

Cys Val

<210> SEQ ID NO 4
<211> LENGTH: 510
<212> TYPE: DNA
<213> ORGANISM: Beta vulgaris
<220> FEATURE:
```

```
<221> NAME/KEY: CDS
<222> LOCATION: (76)..(357)

<400> SEQUENCE: 4
ttataataac tccctctctt acacaaacac ataacataaa tctcctctat acatttttct      60
cttctaagca tcatt atg gcc aag gtg gct act ctt acc cta ctt gcc gtg     111
                Met Ala Lys Val Ala Thr Leu Thr Leu Leu Ala Val
                  1               5                  10 gtt gtc gtg gcg gtg cta cta ttc gag aca cca acg acc gag gcg gtt     159
Val Val Val Ala Val Leu Leu Phe Glu Thr Pro Thr Thr Glu Ala Val
         15                  20                  25 acc tgc agt gca gtg cag ctg agc cct tgc gca cca gca att atg tcc     207
Thr Cys Ser Ala Val Gln Leu Ser Pro Cys Ala Pro Ala Ile Met Ser
 30                  35                  40 aac caa aca cca aca agc gca tgt tgt gca aaa ttg agg gag caa aaa     255
Asn Gln Thr Pro Thr Ser Ala Cys Cys Ala Lys Leu Arg Glu Gln Lys
 45                  50                  55                  60 cct tgc ctt tgt gga tac tac aag aac cct act ctt agg cct tac att     303
Pro Cys Leu Cys Gly Tyr Tyr Lys Asn Pro Thr Leu Arg Pro Tyr Ile
                 65                  70                  75 aat tcc cct ggt gct aaa cgt gtg gct tct act tgt aaa gtc agc gtt     351
Asn Ser Pro Gly Ala Lys Arg Val Ala Ser Thr Cys Lys Val Ser Val
             80                  85                  90 agc tgc taaacatatg taccagtgtt acctaatttg ttatctaatt cgcccaaaat       407
Ser Cys gagccaaaac tgacgataat tagctttcct caattcgtga tttgagggaa attaggtaac    467
tactgatata tataccttcc acaaaacaaa aaaaaaaaaa aaa                      510

<210> SEQ ID NO 5
<211> LENGTH: 94
<212> TYPE: PRT
<213> ORGANISM: Beta vulgaris

<400> SEQUENCE: 5

Met Ala Lys Val Ala Thr Leu Thr Leu Leu Ala Val Val Val Ala
  1               5                  10                  15

Val Leu Leu Phe Glu Thr Pro Thr Thr Glu Ala Val Thr Cys Ser Ala
                 20                  25                  30

Val Gln Leu Ser Pro Cys Ala Pro Ala Ile Met Ser Asn Gln Thr Pro
             35                  40                  45

Thr Ser Ala Cys Cys Ala Lys Leu Arg Glu Gln Lys Pro Cys Leu Cys
         50                  55                  60

Gly Tyr Tyr Lys Asn Pro Thr Leu Arg Pro Tyr Ile Asn Ser Pro Gly
 65                  70                  75                  80

Ala Lys Arg Val Ala Ser Thr Cys Lys Val Ser Val Ser Cys
                 85                  90

<210> SEQ ID NO 6
<211> LENGTH: 92
<212> TYPE: PRT
<213> ORGANISM: Beta vulgaris

<400> SEQUENCE: 6

Ala Ile Asn Cys Gly Leu Val Ser Gln Ser Leu Ala Ala Cys Leu Gly
  1               5                  10                  15

Phe Leu Glu Asn Gly Gln Gly Pro Asn Ala Ala Cys Cys Asn Gly Val
                 20                  25                  30

Lys Thr Leu Arg Asn Leu Thr Pro Thr Thr Gln Asp Lys Arg Thr Ala
```

```
            35                  40                  45
Cys Arg Cys Met Lys Ser Ala Ala Ser Ala Ile Pro Gly Ile Asn His
         50                  55                  60
Lys Tyr Ser Ala Ala Leu Pro Gly Lys Cys Gly Val Ser Ile Pro Gly
 65                  70                  75                  80
Pro Val Gly Pro Gln Ala Asp Cys Ser Gln Ile His
                 85                  90

<210> SEQ ID NO 7
<211> LENGTH: 91
<212> TYPE: PRT
<213> ORGANISM: Beta vulgaris

<400> SEQUENCE: 7

Ile Thr Cys Gly Leu Val Ala Ser Lys Leu Ala Pro Cys Ile Gly Tyr
 1               5                  10                  15
Leu Gln Gly Ala Pro Gly Pro Ser Ala Gly Cys Cys Gly Gly Ile Lys
             20                  25                  30
Gly Leu Asn Ser Ala Ala Ala Ser Pro Ala Asp Arg Lys Thr Ala Cys
         35                  40                  45
Thr Cys Leu Lys Ser Ala Ala Thr Ser Met Lys Gly Ile Asn Tyr Gly
 50                  55                  60
Lys Ala Ala Ser Leu Pro Arg Gln Cys Gly Val Ser Ile Pro Tyr Ala
 65                  70                  75                  80
Ile Ser Pro Asn Thr Asn Cys Asn Ala Ile His
                 85                  90

<210> SEQ ID NO 8
<211> LENGTH: 91
<212> TYPE: PRT
<213> ORGANISM: Beta vulgaris

<400> SEQUENCE: 8

Ile Thr Cys Gly Leu Val Ala Ser Lys Leu Ala Pro Cys Ile Gly Tyr
 1               5                  10                  15
Leu Gln Gly Ala Pro Gly Pro Ser Ala Gly Cys Cys Gly Gly Ile Lys
             20                  25                  30
Gly Leu Asn Ser Ala Ala Ala Ser Pro Ala Asp Arg Lys Thr Ala Cys
         35                  40                  45
Thr Cys Leu Lys Ser Ala Ala Thr Ser Met Lys Gly Ile Asn Tyr Gly
 50                  55                  60
Lys Ala Ala Ser Leu Pro Arg Gln Cys Gly Val Ser Ile Pro Tyr Ala
 65                  70                  75                  80
Ile Ser Pro Asn Thr Asn Cys Asn Ala Ile His
                 85                  90

<210> SEQ ID NO 9
<211> LENGTH: 30
<212> TYPE: PRT
<213> ORGANISM: Beta vulgaris

<400> SEQUENCE: 9

Ser Gly Glu Cys Asn Met Tyr Gly Arg Cys Pro Pro Gly Tyr Cys Cys
 1               5                  10                  15
Ser Lys Phe Gly Tyr Cys Gly Val Gly Arg Ala Tyr Cys Gly
             20                  25                  30

<210> SEQ ID NO 10
```

```
<211> LENGTH: 46
<212> TYPE: PRT
<213> ORGANISM: Beta vulgaris

<400> SEQUENCE: 10

Ala Ile Cys Lys Lys Pro Ser Lys Phe Phe Lys Gly Ala Cys Gly Arg
 1               5                  10                  15
Asp Ala Asp Cys Glu Lys Ala Cys Asp Gln Glu Asn Trp Pro Gly Gly
             20                  25                  30
Val Cys Val Pro Phe Leu Arg Cys Glu Cys Gln Arg Ser Cys
         35                  40                  45

<210> SEQ ID NO 11
<211> LENGTH: 46
<212> TYPE: PRT
<213> ORGANISM: Beta vulgaris

<400> SEQUENCE: 11

Ala Thr Cys Arg Lys Pro Ser Met Tyr Phe Ser Gly Ala Cys Phe Ser
 1               5                  10                  15
Asp Thr Asn Cys Gln Lys Ala Cys Asn Arg Glu Asp Trp Pro Asn Gly
             20                  25                  30
Lys Cys Leu Val Gly Phe Lys Cys Glu Cys Gln Arg Pro Cys
         35                  40                  45

<210> SEQ ID NO 12
<211> LENGTH: 32
<212> TYPE: PRT
<213> ORGANISM: Beta vulgaris

<400> SEQUENCE: 12

Arg Cys Ile Pro Cys Gly Gln Asp Cys Ile Ser Ser Arg Asn Cys Cys
 1               5                  10                  15
Ser Pro Cys Lys Cys Asn Phe Gly Pro Pro Val Pro Arg Cys Thr Asn
             20                  25                  30

<210> SEQ ID NO 13
<211> LENGTH: 549
<212> TYPE: DNA
<213> ORGANISM: Beta vulgaris
<220> FEATURE:
<221> NAME/KEY: CDS
<222> LOCATION: (66)..(293)

<400> SEQUENCE: 13
actcaacaaa ttcagaaaaa aacagaagca aaaaagtttt attgaaagag taagttgagg      60 tgaaa atg atg aaa agc ttt gtg ata gtt atg ttg gtc atg tcc atg atg    110
      Met Met Lys Ser Phe Val Ile Val Met Leu Val Met Ser Met Met
        1               5                  10                  15 gtg gct aca tct atg gca agt ggt gaa tgc aat atg tat ggt cga tgc     158
Val Ala Thr Ser Met Ala Ser Gly Glu Cys Asn Met Tyr Gly Arg Cys
             20                  25                  30 ccc cca ggg tat tgt tgt agc aag ttt ggc tac tgt ggt gtc gga cgc    206
Pro Pro Gly Tyr Cys Cys Ser Lys Phe Gly Tyr Cys Gly Val Gly Arg
         35                  40                  45 gcc tat tgt ggc gat gct gag cag aag gtt gaa gat cat cca tct aat    254
Ala Tyr Cys Gly Asp Ala Glu Gln Lys Val Glu Asp His Pro Ser Asn
     50                  55                  60 gat gct gat gtt cct gag ttt gtt gga gct ggt gcc cca tgatgctcga      303
Asp Ala Asp Val Pro Glu Phe Val Gly Ala Gly Ala Pro
 65                  70                  75
```

-continued

```
agccaggtaa tcgtaatggc atgggttacc taataagtaa actcattgtg cctagcttgc      363
tacatgctta tccactataa ataagctcct acaggagttg tgtttttctt ttaattttgt      423
aatcaagggt ttgactttaa ttaatgagac caatgtatac ttgcatgtcg gataaatatt      483
aactaagcca ctcgtattgg tttattataa aactactata aaaaaaaaaa aaaaaaaaaa      543
aaaaaa                                                                 549
```

<210> SEQ ID NO 14
<211> LENGTH: 76
<212> TYPE: PRT
<213> ORGANISM: Beta vulgaris

<400> SEQUENCE: 14

```
Met Met Lys Ser Phe Val Ile Val Met Leu Val Met Ser Met Met Val
1               5                   10                  15

Ala Thr Ser Met Ala Ser Gly Glu Cys Asn Met Tyr Gly Arg Cys Pro
            20                  25                  30

Pro Gly Tyr Cys Cys Ser Lys Phe Gly Tyr Cys Gly Val Gly Arg Ala
        35                  40                  45

Tyr Cys Gly Asp Ala Glu Gln Lys Val Glu Asp His Pro Ser Asn Asp
    50                  55                  60

Ala Asp Val Pro Glu Phe Val Gly Ala Gly Ala Pro
65                  70                  75
```

<210> SEQ ID NO 15
<211> LENGTH: 52
<212> TYPE: DNA
<213> ORGANISM: Artificial/Unknown
<220> FEATURE:
<221> NAME/KEY: misc_feature
<222> LOCATION: (1)..(52)
<223> OTHER INFORMATION: primer

<400> SEQUENCE: 15

```
ccagtgagca gagtgacgag gactcgagct caagcttttt tttttttttt tt              52
```

<210> SEQ ID NO 16
<211> LENGTH: 18
<212> TYPE: DNA
<213> ORGANISM: Artificial/Unknown
<220> FEATURE:
<221> NAME/KEY: misc_feature
<222> LOCATION: (1)..(18)
<223> OTHER INFORMATION: primer

<400> SEQUENCE: 16

```
ccagtgagca gagtgacg                                                    18
```

<210> SEQ ID NO 17
<211> LENGTH: 18
<212> TYPE: DNA
<213> ORGANISM: Artificial/Unknown
<220> FEATURE:
<221> NAME/KEY: misc_feature
<222> LOCATION: (1)..(18)
<223> OTHER INFORMATION: primer

<400> SEQUENCE: 17

```
gaggactcga gctcaagc                                                    18
```

<210> SEQ ID NO 18
<211> LENGTH: 30
<212> TYPE: DNA

```
<213> ORGANISM: Artificial/Unknown
<220> FEATURE:
<221> NAME/KEY: misc_feature
<222> LOCATION: (1)..(30)
<223> OTHER INFORMATION: primer

<400> SEQUENCE: 18
ggccacgcgt cgactagtac gggggggggg                                           30

<210> SEQ ID NO 19
<211> LENGTH: 21
<212> TYPE: DNA
<213> ORGANISM: Artificial/Unknown
<220> FEATURE:
<221> NAME/KEY: misc_feature
<222> LOCATION: (1)..(21)
<223> OTHER INFORMATION: primer

<400> SEQUENCE: 19
ggccacgcgt cgactagtac g                                                    21

<210> SEQ ID NO 20
<211> LENGTH: 17
<212> TYPE: DNA
<213> ORGANISM: Artificial/Unknown
<220> FEATURE:
<221> NAME/KEY: misc_feature
<222> LOCATION: (1)..(17)
<223> OTHER INFORMATION: primer
<221> NAME/KEY: misc_feature
<222> LOCATION: (1)..(17)
<223> OTHER INFORMATION: n = a, t, c, or g

<400> SEQUENCE: 20
gcntgymgnt gyatgaa                                                         17

<210> SEQ ID NO 21
<211> LENGTH: 17
<212> TYPE: DNA
<213> ORGANISM: Artificial/Unknown
<220> FEATURE:
<221> NAME/KEY: misc_feature
<222> LOCATION: (1)..(17)
<223> OTHER INFORMATION: primer
<221> NAME/KEY: misc_feature
<222> LOCATION: (1)..(17)
<223> OTHER INFORMATION: n = a, t, c, or g

<400> SEQUENCE: 21
ggnathaayc ayaarta                                                         17

<210> SEQ ID NO 22
<211> LENGTH: 21
<212> TYPE: DNA
<213> ORGANISM: Artificial/Unknown
<220> FEATURE:
<221> NAME/KEY: misc_feature
<222> LOCATION: (1)..(21)
<223> OTHER INFORMATION: primer

<400> SEQUENCE: 22
tggaattgga gattatgtaa g                                                    21

<210> SEQ ID NO 23
<211> LENGTH: 27
<212> TYPE: DNA
<213> ORGANISM: Artificial/Unknown
<220> FEATURE:
<221> NAME/KEY: misc_feature
```

```
<222> LOCATION: (1)..(27)
<223> OTHER INFORMATION: primer

<400> SEQUENCE: 23
tcactttaga tgtaagaagc acacatg                                              27

<210> SEQ ID NO 24
<211> LENGTH: 25
<212> TYPE: DNA
<213> ORGANISM: Artificial/Unknown
<220> FEATURE:
<221> NAME/KEY: misc_feature
<222> LOCATION: (1)..(25)
<223> OTHER INFORMATION: primer

<400> SEQUENCE: 24
taagcagaaa gttccagaaa gcatg                                                25

<210> SEQ ID NO 25
<211> LENGTH: 17
<212> TYPE: DNA
<213> ORGANISM: Artificial/Unknown
<220> FEATURE:
<221> NAME/KEY: misc_feature
<222> LOCATION: (1)..(17)
<223> OTHER INFORMATION: primer
<221> NAME/KEY: misc_feature
<222> LOCATION: (1)..(17)
<223> OTHER INFORMATION: n = a, t, c, or g

<400> SEQUENCE: 25
ggntaytgya ayathyt                                                         17

<210> SEQ ID NO 26
<211> LENGTH: 17
<212> TYPE: DNA
<213> ORGANISM: Artificial/Unknown
<220> FEATURE:
<221> NAME/KEY: misc_feature
<222> LOCATION: (1)..(17)
<223> OTHER INFORMATION: primer
<221> NAME/KEY: misc_feature
<222> LOCATION: (1)..(17)
<223> OTHER INFORMATION: n = a, t, c, or g

<400> SEQUENCE: 26
aaygtntgyt gygcngg                                                         17

<210> SEQ ID NO 27
<211> LENGTH: 25
<212> TYPE: DNA
<213> ORGANISM: Artificial/Unknown
<220> FEATURE:
<221> NAME/KEY: misc_feature
<222> LOCATION: (1)..(25)
<223> OTHER INFORMATION: primer

<400> SEQUENCE: 27
catcaagaag tccataattg tctag                                                25

<210> SEQ ID NO 28
<211> LENGTH: 24
<212> TYPE: DNA
<213> ORGANISM: Artificial/Unknown
<220> FEATURE:
<221> NAME/KEY: misc_feature
<222> LOCATION: (1)..(24)
<223> OTHER INFORMATION: primer
```

<400> SEQUENCE: 28
tgatctttat tgacaaacag acgc     24

<210> SEQ ID NO 29
<211> LENGTH: 27
<212> TYPE: DNA
<213> ORGANISM: Artificial/Unknown
<220> FEATURE:
<221> NAME/KEY: misc_feature
<222> LOCATION: (1)..(27)
<223> OTHER INFORMATION: primer

<400> SEQUENCE: 29
acagacacgc tagttagatg actaagc     27

<210> SEQ ID NO 30
<211> LENGTH: 18
<212> TYPE: DNA
<213> ORGANISM: Artificial/Unknown
<220> FEATURE:
<221> NAME/KEY: misc_feature
<222> LOCATION: (1)..(18)
<223> OTHER INFORMATION: primer
<221> NAME/KEY: misc_feature
<222> LOCATION: (1)..(18)
<223> OTHER INFORMATION: n = a, t, c, or g

<400> SEQUENCE: 30
garcaraarc cntgayyt     18

<210> SEQ ID NO 31
<211> LENGTH: 17
<212> TYPE: DNA
<213> ORGANISM: Artificial/Unknown
<220> FEATURE:
<221> NAME/KEY: misc_feature
<222> LOCATION: (1)..(17)
<223> OTHER INFORMATION: primer
<221> NAME/KEY: misc_feature
<222> LOCATION: (1)..(17)
<223> OTHER INFORMATION: n = a, t, c, or g

<400> SEQUENCE: 31
tgyggntayt ayaaraa     17

<210> SEQ ID NO 32
<211> LENGTH: 21
<212> TYPE: DNA
<213> ORGANISM: Artificial/Unknown
<220> FEATURE:
<221> NAME/KEY: misc_feature
<222> LOCATION: (1)..(21)
<223> OTHER INFORMATION: primer

<400> SEQUENCE: 32
cctaatttcc ctcaaatcac g     21

<210> SEQ ID NO 33
<211> LENGTH: 25
<212> TYPE: DNA
<213> ORGANISM: Artificial/Unknown
<220> FEATURE:
<221> NAME/KEY: misc_feature
<222> LOCATION: (1)..(25)
<223> OTHER INFORMATION: primer

<400> SEQUENCE: 33
aatttccctc aaatcacgaa ttgag     25

```
<210> SEQ ID NO 34
<211> LENGTH: 24
<212> TYPE: DNA
<213> ORGANISM: Artificial/Unknown
<220> FEATURE:
<221> NAME/KEY: misc_feature
<222> LOCATION: (1)..(24)
<223> OTHER INFORMATION: primer

<400> SEQUENCE: 34
tcgtcagttt tggctcattt tggg                                              24

<210> SEQ ID NO 35
<211> LENGTH: 15
<212> TYPE: PRT
<213> ORGANISM: Beta vulgaris
<220> FEATURE:
<221> NAME/KEY: SITE
<222> LOCATION: (1)..(1)
<223> OTHER INFORMATION: Xaa = Gln or Cys
<221> NAME/KEY: SITE
<222> LOCATION: (2)..(2)
<223> OTHER INFORMATION: Xaa = any amino acid except cysteine
<221> NAME/KEY: SITE
<222> LOCATION: (3)..(3)
<223> OTHER INFORMATION: Xaa = Pro or Ile
<221> NAME/KEY: SITE
<222> LOCATION: (4)..(4)
<223> OTHER INFORMATION: Xaa = Asn, Thr, or Leu, except that Xaa is Leu
      when AA1 is Cys
<221> NAME/KEY: SITE
<222> LOCATION: (5)..(5)
<223> OTHER INFORMATION: Xaa = any amino acid
<221> NAME/KEY: SITE
<222> LOCATION: (6)..(6)
<223> OTHER INFORMATION: Xaa = any amino acid
<221> NAME/KEY: SITE
<222> LOCATION: (9)..(9)
<223> OTHER INFORMATION: Xaa = Ala or Asn
<221> NAME/KEY: SITE
<222> LOCATION: (10)..(10)
<223> OTHER INFORMATION: Xaa = Gly or Lys
<221> NAME/KEY: SITE
<222> LOCATION: (11)..(11)
<223> OTHER INFORMATION: Xaa = any amino acid
<221> NAME/KEY: SITE
<222> LOCATION: (12)..(12)
<223> OTHER INFORMATION: Xaa = any amino acid
<221> NAME/KEY: SITE
<222> LOCATION: (13)..(13)
<223> OTHER INFORMATION: Xaa = any amino acid
<221> NAME/KEY: SITE
<222> LOCATION: (14)..(14)
<223> OTHER INFORMATION: Xaa = any amino acid except cysteine
<221> NAME/KEY: SITE
<222> LOCATION: (15)..(15)
<223> OTHER INFORMATION: Xaa = any amino acid

<400> SEQUENCE: 35

Xaa Xaa Xaa Xaa Xaa Xaa Cys Cys Xaa Xaa Xaa Xaa Xaa Xaa Xaa
1               5                   10                  15
```

ANTIMICROBIAL PROTEINS

This application is a § 371 of PCT/EP96/05765, filed Dec. 20, 1996, which claims priority to GB 9526238.2, filed Dec. 21, 1995.

The present invention relates to anti-microbial proteins isolatable from sugar beet.

According to the present invention there is provided anti-microbial protein comprising a peptide having the sequence -Gln/Cys-$AA_2$-Pro/Ile-Asn/Thr/Leu-$AA_5$-AA-Cys-Cys-Ala/Asn-Gly/Lys-$AA_{11}$-$AA_{12}$-$AA_{13}$-$AA_{14}$-$AA_{15}$-(SEQ ID NO: 35), with the proviso that $AA_2$ and $AA_{14}$ are not cysteine, and that $AA_4$ is Leu when $AA_1$ is Cys. The skilled man will recognize that the abbreviation $AA_x$ means one of the 20 commonly occurring amino acids.

An anti-microbial protein includes a protein (alone or in combination with another material) which is toxic or growth inhibitory under any circumstances to any micro-organism, including bacteria, (most particularly Gram positive bacteria), viruses and particularly fungi. Such anti-microbial proteins include those that exhibit anti-microbial activity upon contact with a micro-organism and those that are anti-microbial as a consequence of assimilation or respiration thereof.

According to the present invention there is provided an anti-microbial protein having the sequence depicted in any one of SEQ ID Nos. 3, 5 or 6.

Also included is an isoform of an anti-microbial protein having SEQ ID No. 3 wherein Val in pos. 80 is Ala.

The invention still further includes pure protein which is substantially similar to any one of the above mentioned proteins.

By "substantially similar" is meant pure proteins comprising an amino acid sequence which ist at least 95% similar to the peptide sequence given above (also as defined in claim 1) and/or pure proteins having an amino acid sequence which is at least 65% similar, preferably 75% similar, more preferred 85% similar, particularly preferred 95% similar to the sequence of the proteins depicted in SEQ ID Nos 3, 5 or 6 below. In the context of the present invention, two amino acid sequences with a given percentage similarity to each other have at least that percentage of identical or conservatively replaced amino acid residues in a like position when aligned optimally allowing for up to 2 gaps with the proviso that in respect of each gap a total not more than 2 amino acid residues is affected.

For the purpose of the present invention conservative replacements may be made between amino acids within the following groups:

(i) Serine and Threonine;
(ii) Glutamic acid and Aspartic acid;
(iii) Arginine and Lysine;
(iv) Asparagine and Glutamine;
(v) Isoleucine, Leucine, Valine and Methionine;
(vi) Phenylalanine, Tyrosine and Tryptophan
(vii) Alanine and Glycine The invention still further includes pure proteins which are at least 90% identical to the anti-microbial proteins according to the invention, as well as pure proteins which have at least 90% of the specific activity thereof. For the purposes of the present application, specific activity is a measurement of the amount of growth or replication inhibition produced by a specified quantity of the protein on a specified quantity of a specified micro-organism.

The invention still further includes said pure proteins in combination with at least one protein selected from the group consisting of those depicted in SEQ ID Nos. 7 to 12 and 14. Such combined proteins may be further combined with one or more of the known "pathogenesis-related proteins". Infection of plants with fungal or viral pathogens may induce a systemic synthesis of about 10 families of homologous pathogenesis-related proteins (PR proteins) in vegetative tissues. Such PR-proteins have been classified into 5 groups. The PR-2, PR-3 and PR-5 proteins are beta-1,3-glucanase, chitinases and thaumatin-like proteins respectively. Specific functions have not been assigned to the PR-1 and PR-4 groups of proteins. The PR4 proteins are similar to C-terminal domains of prohevein and the putative wound-induced WIN proteins of potato, thus lacking the N-terminal hevein domain. It is particularly preferred that the proteins according to the invention are combined with one or more proteins which are the basic counter parts of the P-R 4 group of proteins, meaning the basic counter part of proteins similar to the C-terminal domains of prohevein and the putative wound-induced WIN proteins of potato. It is particularly preferred that the basic counter-part of the said pathogenesis-related proteins is a chitin-binding WIN protein, in particular that produced by barley grain or stressed barley leaves.

The invention still further includes recombinant DNA comprising a sequence encoding a protein having the amino acid sequence of the above disclosed anti-microbial proteins. In particular the DNA may encode at least one of the proteins the sequences of which are depicted in SEQ ID Nos. 3, 5 and 6, optionally in addition to at least one of the proteins the sequences of which are depicted in SEQ ID Nos. 7 to 12 and 14. Preferably the sequence encoding a protein having the amino acid sequence depicted in SEQ ID No. 3, 5 or 6 has the cDNA sequence depicted in SEQ ID No. 1 (for the protein with SEQ ID No. 6, corresponding to IWF5), in SEQ ID No. 2 (for the protein with SEQ ID No. 3, corresponding to IWF6) or in SEQ ID No. 4 (for the protein with SEQ ID No. 5, corresponding to IWF7). The recombinant DNA may further encode a protein having herbicide resistance, plant growth-promoting, anti-fungal, anti bacterial, anti-viral and/or anti-nematode properties. In the case that the DNA is to be introduced into a heterologous organism it may be modified to remove known mRNA instability motifs (such as AT-rich regions) and polyadenylation signals (if any are present). and/or codons which are preferred by the organism into which the recombinant DNA is to be inserted may be used so that expression of the thus modified DNA in the said organism yields substantially similar protein to that obtained by expression of the unmodified recombinant DNA in the organism in which the anti-microbial protein according to the invention is endogenous.

The invention still further includes recombinant DNA which is "similar" to that mentioned above. By "similar DNA" is meant a sequence which is complementary to a test sequence which is capable of hybridizing to the inventive recombinant sequence. When the test and inventive sequences are double stranded the nucleic acid constituting the test sequence preferably has a TM within 20° C. of that of the inventive sequence. In the case that the test and inventive sequences are mixed together and denatured simultaneously, the TM values of the sequences are preferably within 10° C. of each other. More preferably the hybridization is performed under stringent conditions, with either the test or inventive DNA preferably being supported. Thus either a denatured test or inventive sequence is preferably first bound to a support and hybridization is effected for a specified period of time at a temperature of between 50 and 70° C. in double strength citrate buffered saline (SSC)

containing 0.1% SDS followed by rinsing of the support at the same temperature but with a buffer having a reduced SSC concentration. Depending upon the degree of stringency required, and thus the degree of similarity of the sequences, at a particular temperature,—such as 60° C., for example—such reduced concentration buffers are typically single strength SSC containing 0.1% SDS, half strength SSC containing 0.1% SDS and one tenth strength SSC containing 0.1% SDS. Sequences having the greatest degree of similarity are those the hybridization of which is least affected by washing in buffers of reduced concentration. It is most preferred that the test and inventive sequences are so similar that the hybridization between them is substantially unaffected by washing or incubation in one tenth strength sodium citrate buffer containing 0.1% SDS.

The invention still further includes a DNA sequence which is complementary to one which hybridizes under stringent conditions with the recombinant DNA according to the invention.

Also included in the present invention is: a vector which contains the above disclosed DNA which is expressible in plants and linked to a plant operable promoter and terminator; plants transformed with such DNA; the progeny of such plants which contain the DNA stably incorporated and hereditable in a Mendelian manner, and/or the seeds of such plants and such progeny. The transformed plants are made by known methods and include regeneration of plant cells or protoplasts transformed with the DNA of the invention according to a variety of known methods (Agrobacterium Ti and Ri plasmids, electroporation, micro-injection, micro-projectile gun etc). The transformed cell may in suitable cases be regenerated into whole plants in which the nuclear material is stably incorporated into the genome. Both monocot and dicot plants may be obtained in this way. Examples of transformed plants according to the present invention include: fruits, including tomatoes, mangoes, peaches, apples, pears, strawberries, bananas, and melons; field cops such as canola, sunflower, tobacco, sugar beet, small grain cereals such as wheat, barley and rice, maize and cotton, and vegetables such as potato, carrot, lettuce, cabbage and onion. The preferred plants are sugar beet and maize. The invention still further includes protein derived from expression of the said DNA, and anti-microbial protein produced by expression of the recombinant DNA within plants transformed therewith.

The invention still further includes an anti-microbial composition containing one or more of the proteins according to the invention; a process for combatting fungi which comprises exposing them to such proteins, and an extraction process for obtaining anti-microbial proteins from organic material containing them comprising submitting the material—preferably in the form of a micro-organism—to maceration and solvent extraction. It will be appreciated that the anti-microbial protein exhibits little, if any, anti-microbial effect on the micro-organism which is the source of the organic material referred to in the previous sentence.

The invention will be further apparent from the following description and the associated drawings and sequence listings.

Figure 4:
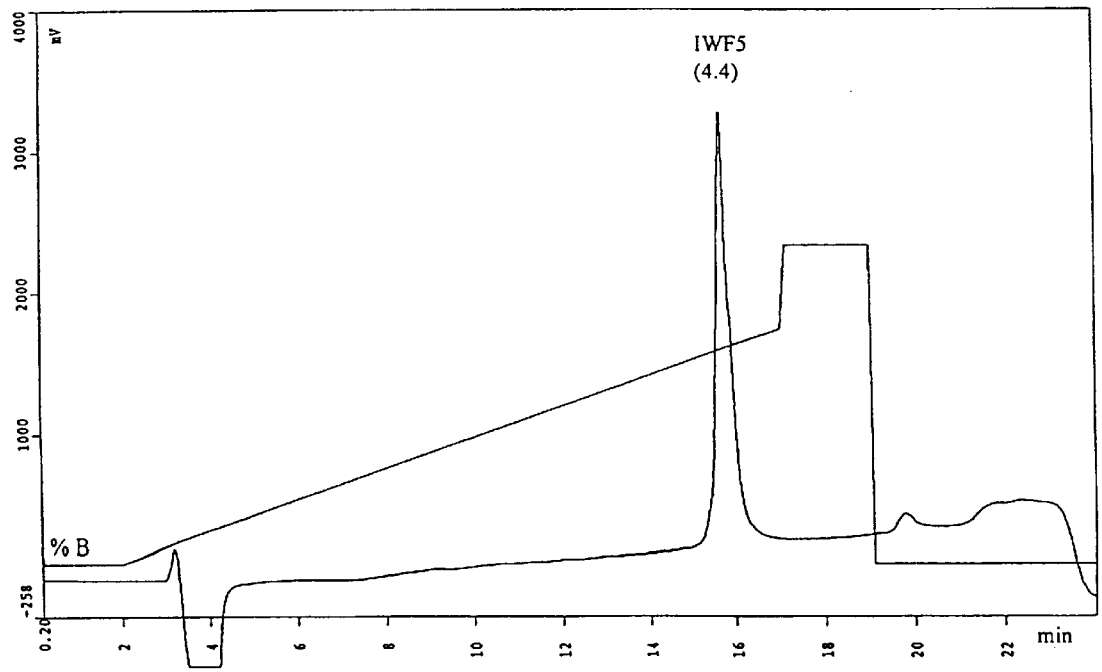
FIG. 4 shows a typical elution profile from an RP-HPLC column of the protein represented by peak 4.4 in FIG. 3.

SEQ ID No. 6 shows the amino acid sequence of protein represented by peak 4.4 in FIG. 4; SEQ ID No. 3 wherein Val in pos. 80 is Ala shows the amino acid sequence of protein represented by peak 4.3 in FIG. 5; and SEQ ID No. 5 shows the amino acid sequence of protein represented by peak 5.4 in FIG. 7; SEQ ID Nos. 7 to 12 and 14 show the amino acid sequences of known anti-fungal proteins.

Induction of Resistance

Six-week old plants of sugar beet (*Beta vulgaris* L., cv. Monova, Danisco Seed) are treated four times with 25 ppm 2,6-dichloroisonicotinic acid (INA) with a two-day interval. The INA, suspended in 0.05% Tween 20, is applied by spraying the adaxial leaf surface to the point of saturation. Two days after the final treatment, intercellular washing fluid (IWF) is isolated as described below. Intercellular washing fluid isolated from leaves not subjected to INA also contains proteins according to the present invention.

Isolation of Intercellular Washing Fluid

IWF is isolated from 500–700 gram sugar beet leaves by submerging them in 20 mM HAc (pH 4.5). The thus submerged leaves are then placed in an exicator and vacuum infiltrated for 5 min at 4 torr (max). Following air-drying of the leaf surface, the IWF is collected by centrifugation at 500 g for 15 min in 500 ml centrifuge tubes.

Cation Exchange Chromatography

The thus obtained IWF is fractionated by cation exchange chromatography on a 10 ml CM-Sepharose column (Pharmacia LKB) pre-equilibrated in starting buffer (20 mM HAc (pH 4.5)). The fractionation is performed at 4° C. at a flow rate of 25 ml/h. Fractions of 3 ml are collected. Proteins not bound to the column are removed by extensive washing of the column with starting buffer. Bound proteins are eluted by applying to the column further starting buffer comprising stepwise increased salt concentrations: viz, 0.1 M NaCl, 0.3 M NACl and 0.5 M NaCl. The absorbance at 280 nm of the eluate is measured, and fractions judged to comprise protein are tested for their anti-fungal activity against *Cercospora beticola* using the microtiter plate bioassay described previously (PCT Patent Application No. PCT/DK92/00108, Publication No. WO 92/17591, now assigned to Sandoz LTD).

Figure 1:
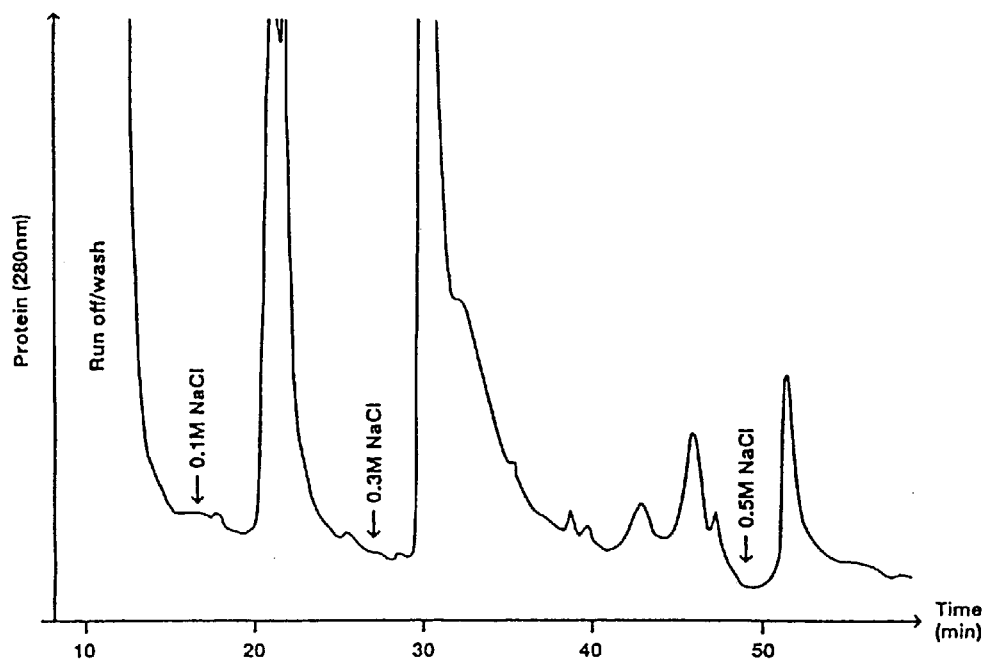
FIG. 1 shows a typical elution profile of intercellular washing fluid from a CM-Sepharose column.

A typical elution profile is shown in FIG. 1. The eluates resulting from application to the column of starting buffer comprising the 0.3M NaCl is further purified as described below.

Purification of Antifungal Proteins in the 0.3 M NaCl Eluate from the CM-Sepharose. FPLC Chromatography The 0.3M NaCl protein fraction is desalted by overnight dialysis (MW cut off: 1 kDa) against 20 mM HAc (pH 4.5) at 4° C. Betaine is added at a concentration of 5% (w/v) to the thus dialysed protein fraction. Four ml of the resulting solution is then fractionated by cation exchange fast protein liquid chromatography (FPLC) using a Mono S HR 5/5 column (Pharmacia LKB) equilibrated in 20 mM HAc (pH 4.5) containing 5% (w/v) betaine (A-buffer). Bound proteins are eluted with a linear salt gradient from 0 to 0.3 M NaCl in 30 ml of the A-buffer followed by a step elution with 1.0 M NaCl in the same buffer. Flow rate is 1 ml/min.

Figure 2:
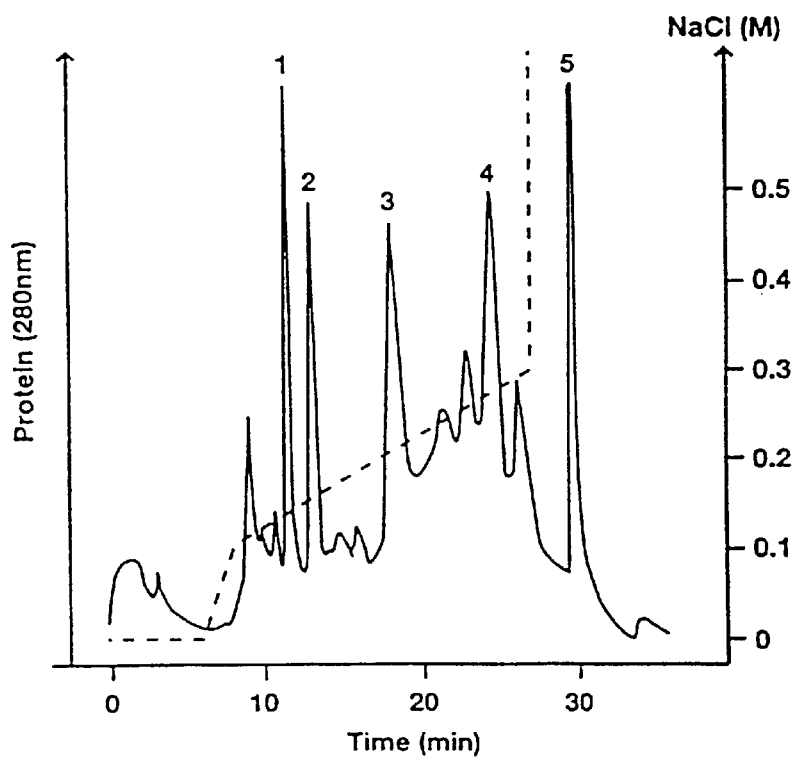
FIG. 2 shows a typical elution profile from a Mono S FPLC column of the 0.3M NaCl fraction shown in FIG. 1.

FIG. 2 shows that the 0.3M NaCl fraction contains a number of distinct proteins, the quantitatively most significant of which are designated as peaks 1–5. Strong antifungal activity is associated with the proteins represented by peaks 4 and 5. When separated by SDS-PAGE using the Phast System (Pharmacia LKB), silver stained 10–15% gradient Phast gels or High Density gels (Pharmacia LKB) reveal that each of the peaks 4 and 5 contains about 10 different proteins.

Reverse Phase HPLC

Figure 3:
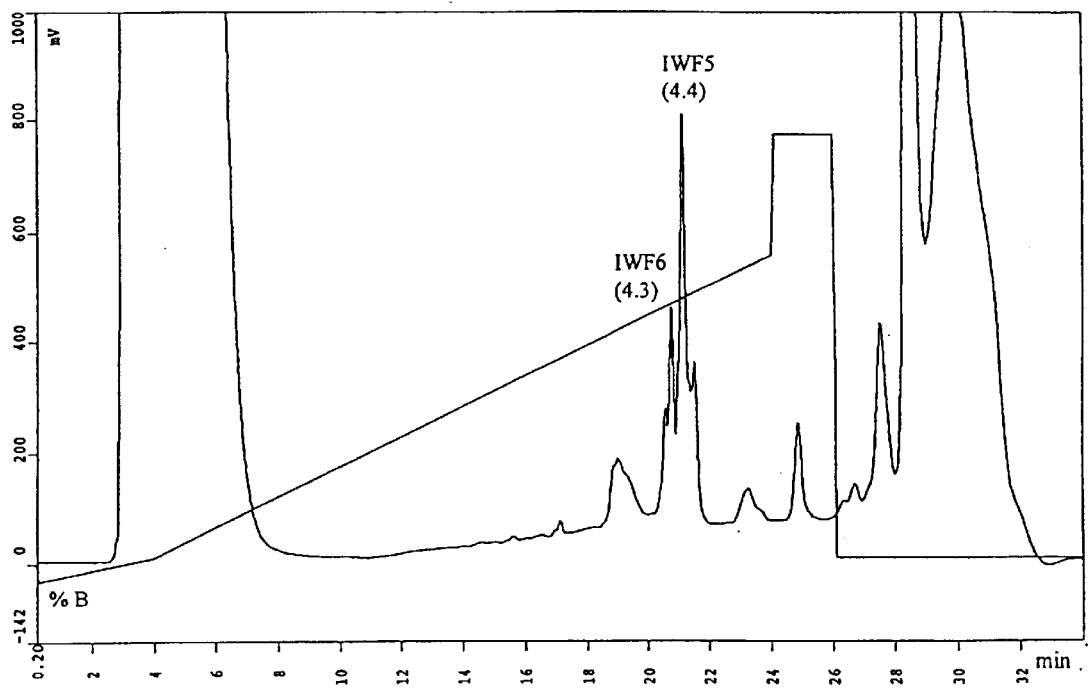
FIG. 3 shows a typical elution profile from an RP-HPLC column of the proteins represented by peak 4 in FIG. 2.
Figure 5:
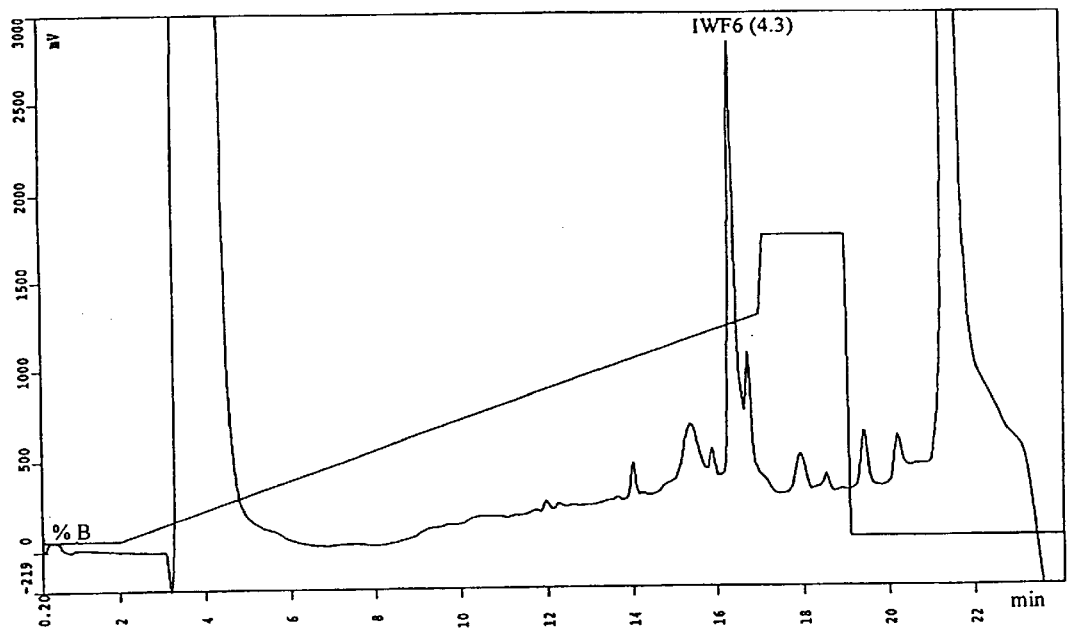
FIG. 5 shows a typical elution profile from an RP-HPLC column of the protein represented by peak 4.3 in FIG. 3.
Figure 6:
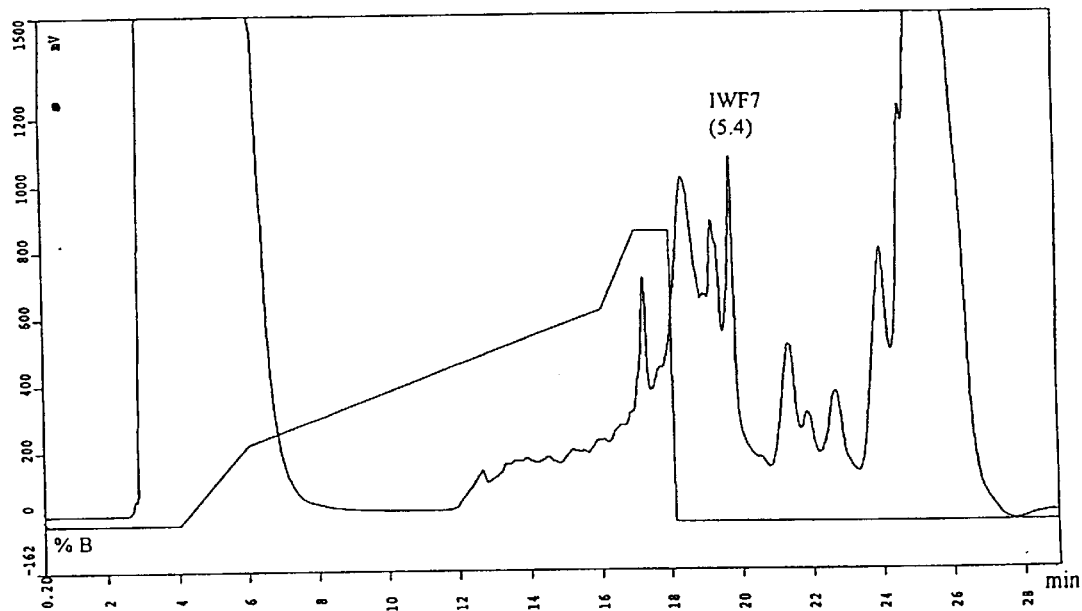
FIG. 6 shows a typical elution profile from an RP-HPLC column of the protein represented by peak 5 in FIG. 2.

Protein peaks 4 and 5 (depicted in FIG. 2) from the Mono S column is further purified by reverse phase (RP-) HPLC on a Vydac $C_4$ silica column (The Separations Group, CA, USA). The solvent system is A: 0.1% TFA in water and B: 0.1% TFA in acetonitrile. Proteins are eluted with a linear gradient of 5 to 45% of the B-buffer applied in 18 min after sample loading followed by 60% B-buffer in 2 min. Flow rate is 0.7 ml/min. Protein is detected by monitoring the absorbance of the eluate at 214 and 280 nm. Discrete protein peaks are collected and lyophilized. The thus lyophilized proteins are washed twice with water, re-lyophilized and subsequently resolved in 10 mM Tris-HCl (pH 8.0), prior to analysis of purity and anti-fungal activity. The material represented by peak 4 is separated into 9–10 distinct protein peaks (FIG. 3) on the RP-HPLC column. Peaks 4.3 and 4.4 comprise strong antifungal activity and are consequently re-chromatographed on the RP-C4 column (FIGS. 4 and 5). A subsequent analysis by SDS-PAGE (silver staining) demonstrated that these two proteins had been purified to homogeneity (data not shown). Furthermore, the N-terminal amino acid sequencing confirmed the presence of only one protein in each peak. Peak 4.3 and 4.4 are designated IWF6 and IWF5, respectively. The material represented by peak 5 in FIG. 2 is separated into 8–10 different protein peaks following RP-HPLC purification (FIG. 6). Of these, peak 5.4 comprised strong antifungal activity. Following a 2nd round of RP-HPLC (FIG. 7), the protein was homogenous as confirmed by SDS-PAGE and amino acid sequencing. This protein is designated IWF7.

Antifungal Activity

Figure 8:
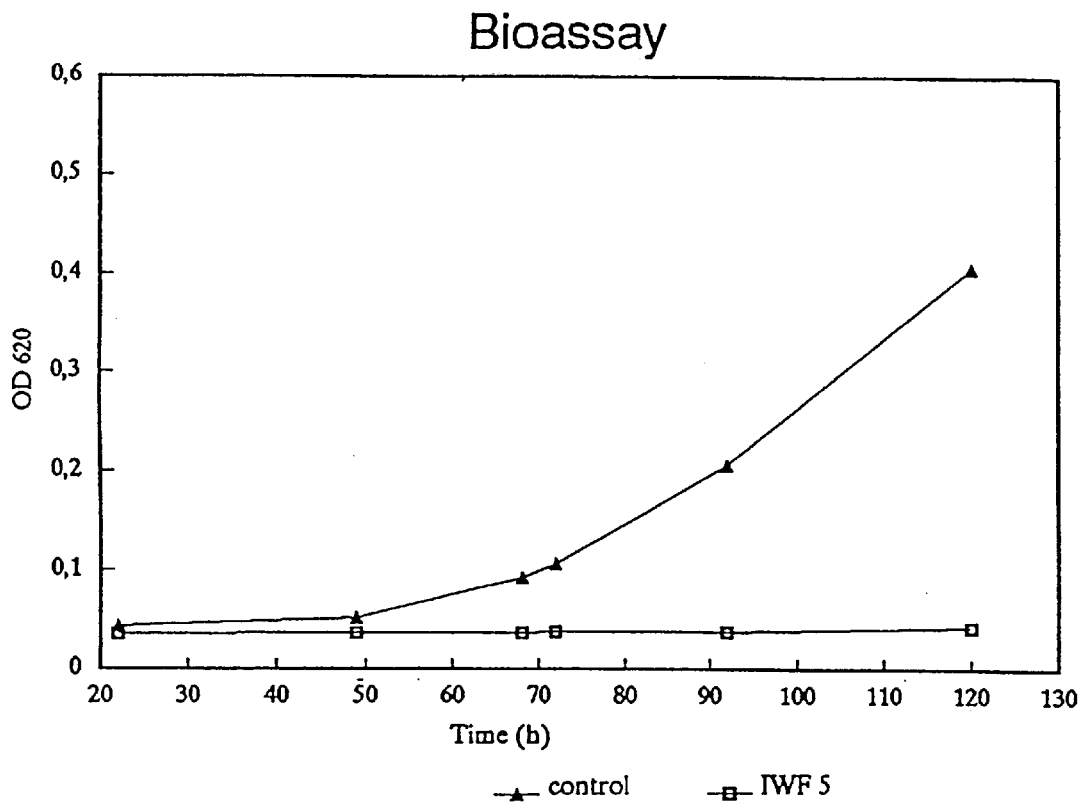
FIGS. 8 and 9 show the anti-fungal activity of various amounts of the protein represented by peak 4.4 in FIG. 4 (SEQ ID No. 6)
Figure 9:
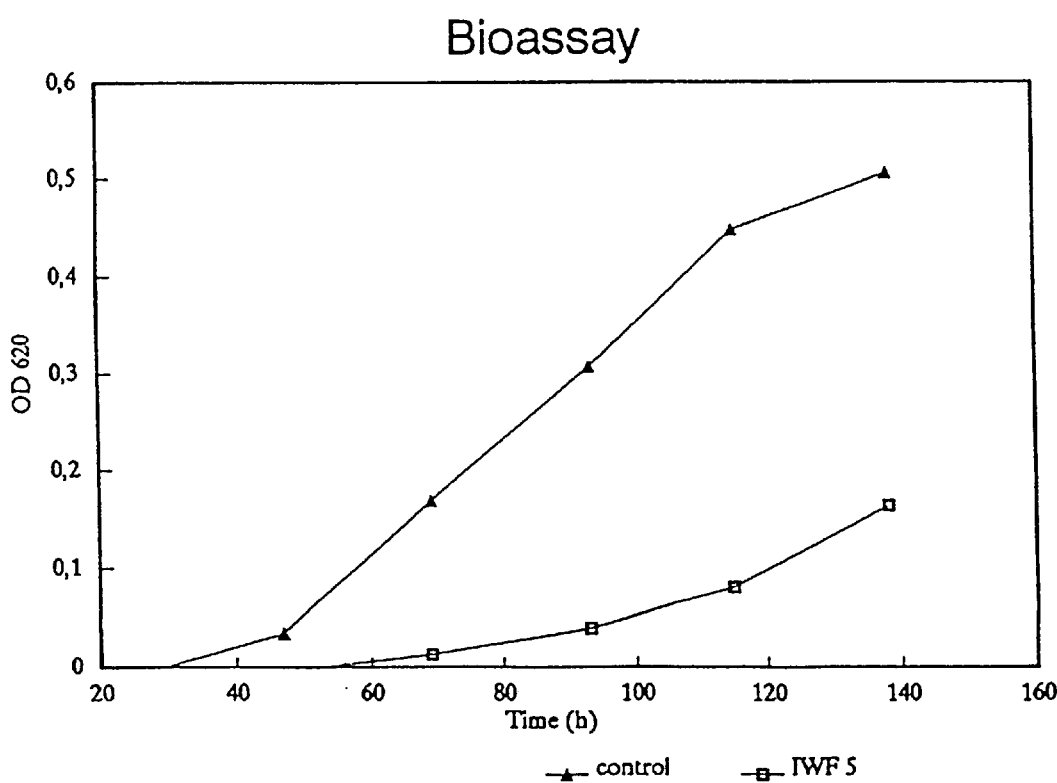
Figure 10:
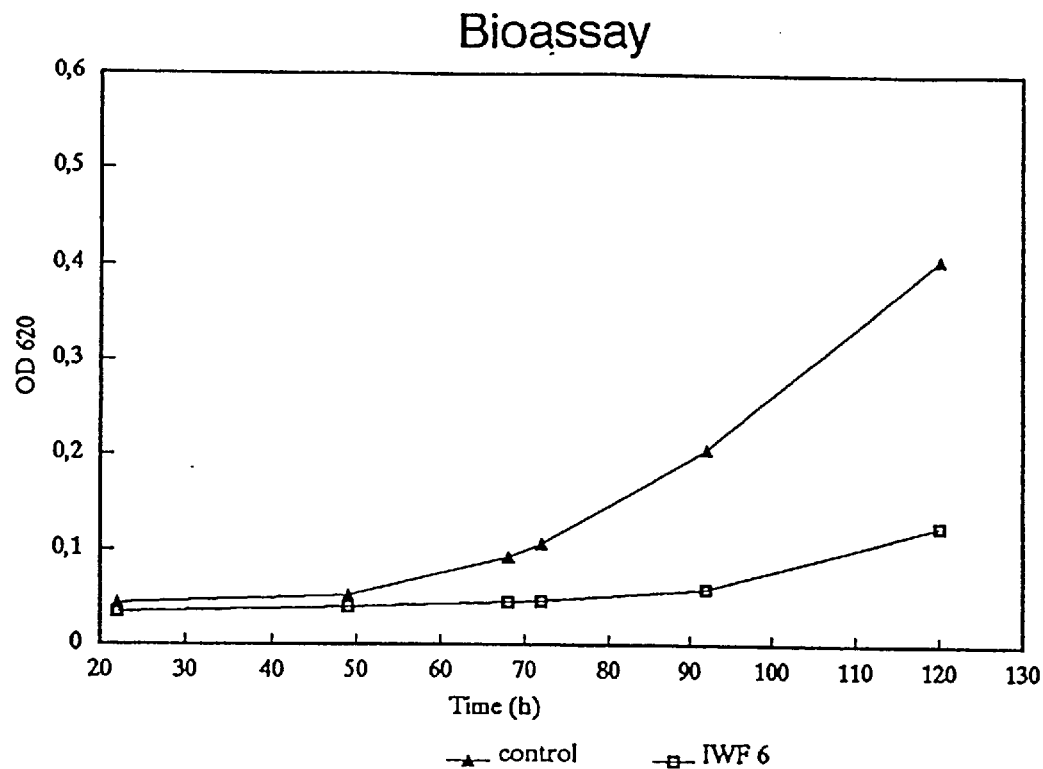
FIG. 10 shows the anti-fungal activity of the protein represented by peak 4.3 (SEQ ID No. 3 wherein Val in pos 80 is Ala) in FIG. 5.

The proteins, either alone or in combination with WIN N (which is purified from barley grain or stressed barley leaf as described by Hejgaard et al (FEBS Letters, 307, 389–392 (1992)), and/or a protein having a sequence corresponding to at least one of those given in SEQ ID Nos. 7–12 and 14, are incubated with spores of *C. beticola*. The assay mix (240 ul) contains 100 ul of potato dextrose broth (Difco), 40 ul protein sample (or buffer control) in 100 mM Tris and 20 mM NaCl (pH 8.0) as well as approximately 400 spores in 100 ul water. The micro-titre plates are sealed with tape to avoid evaporation and contamination and subsequently incubated at room temperature on an agitator operated at 200 rpm. The absorbance at 620 nm is measured each day for 8 days and plotted for each concentration of protein vs time. The protein designated as IWF 5 showed a strong growth inhibiting effect against *C. beticola*. At 10 μg/well (40 μg/ml) no fungal growth could be detected (FIG. 8) and at 4)ig/well the growth was markedly delayed and strongly inhibited (FIG. 9). The protein designated as JWF6 also shows a strong growth inhibiting effect against *C. beticola*. The level of activity is comparable to that of PWF5, giving almost complete growth inhibition at ~5 μg/well (FIG. 10).

Figure 11:
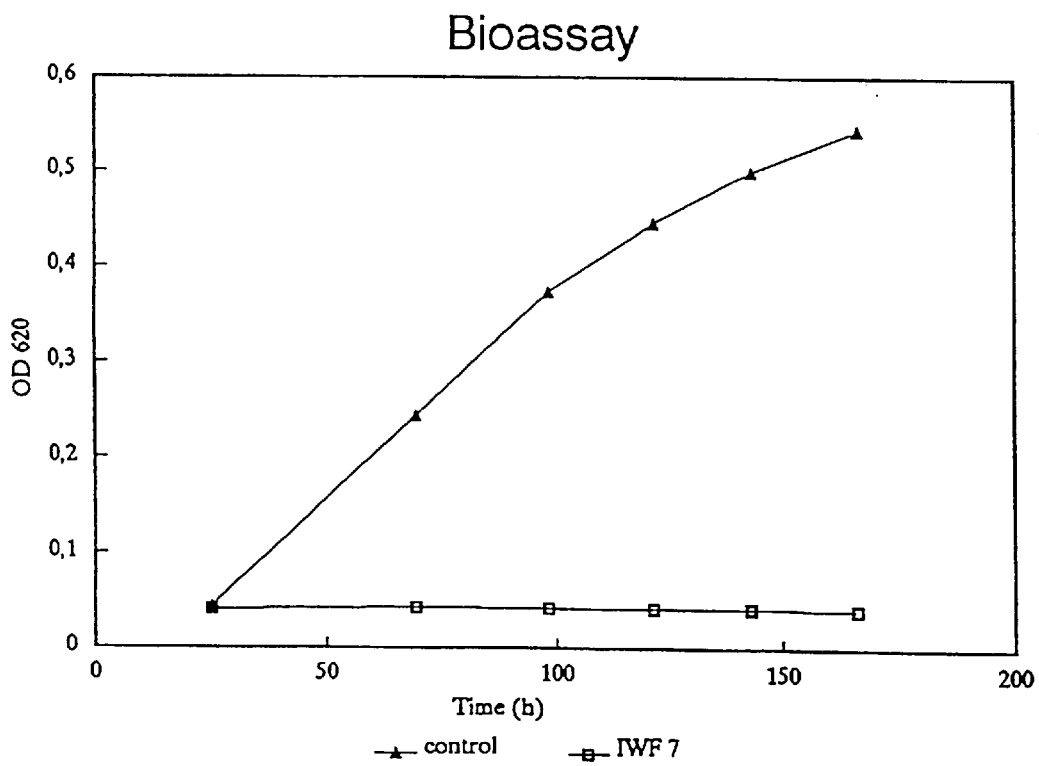
FIG. 11 shows the anti-fungal activity of the protein represented by peak 5.4 (SEQ ID No. 5) in FIG. 7.

Moreover, the protein designated as IWF7 also shows a strong growth inhibiting effect against *C. beticola*. At 10 μg/well no fungal growth was detected (FIG. 11). Furthermore, microscopical analyses indicated that the protein inhibited the germination of conidia. Thus, IWF7 may effect spore germination as well as hyphal growth.

Amino Acid Sequencing

Figure 7:
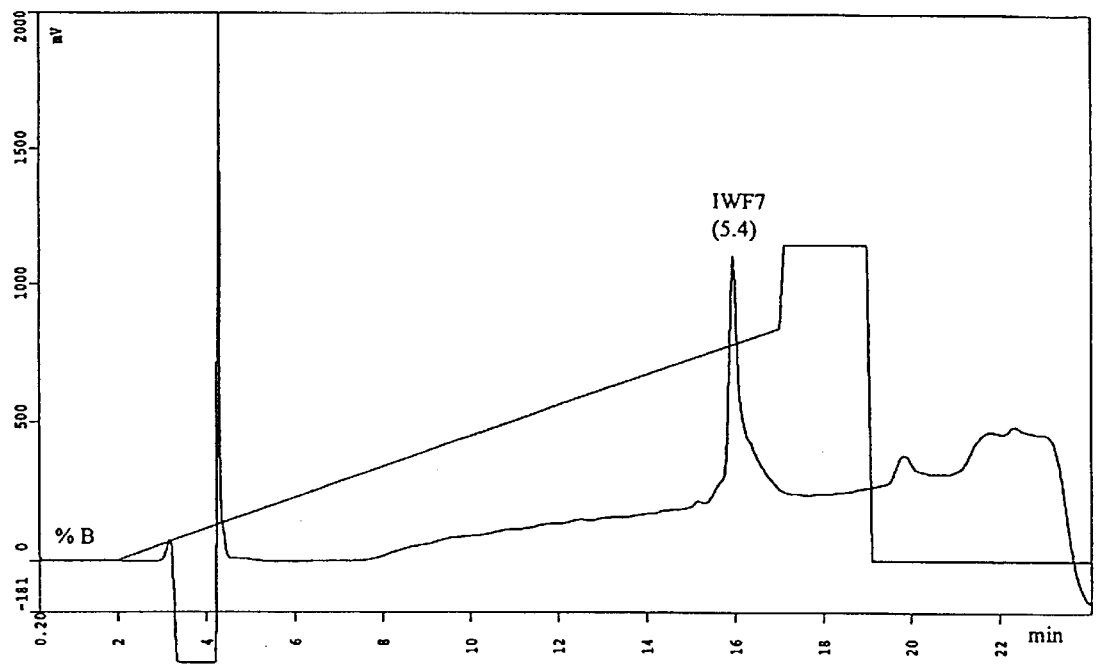
FIG. 7 shows a typical elution profile from an RP-HPLC column of the protein represented by peak 5.4 in FIG. 6.

The purified anti-fungal proteins corresponding to peak 4.4 in FIG. 4, peak 4.3 in FIG. 5 and peak 4.4 in FIG. 7 which originate from the 0.3 M NaCl eluate from the CM-Sepharose column, (FIG. 1); are carboxymethylated and subjected to RP-HPLC on a Vydac C, column. The solvent system is A: 0.1% TFA in water and B: 0.1% TFA in acetonitrile. The proteins elute as single peaks with slightly different retention times. The C-terminal sequences of the proteins are obtained by cleavage thereof with endo-R-proteinase and subsequent purification by RP-HPLC on a Vydac $C_{18}$ column.

Cloning of IWF5, IWF6 and IWF/cDNA

The cDNA sequence of IWF5, IWF6 and IWF7 was obtained by 3' and 5' RACE as described previously (Nielsen et al. 1996; Plant Mol. Biol., 31:539–552) using the following primers.

A. 3' RACE Primers.

$Q_T$:
  5'-CCAGTGAGCAGAGTGACGAGGACTCGAGCTC-AAGC(T)$_{17}$-3' (SEQ ID NO: 15)
$Q_0$: 5'-CCAGTGAGCAGAGTGACG-3' (SEQ ID NO: 16)
$Q_1$: GAGGACTCGAGCTCAAGC-3'(SEQ ID NO: 17)

B. 5' RACE primers.
5'-ANKER:
  5'-GGCCACGCGTCGACTAGTACGGGGGGGGGG-3' (SEQ ID NO: 18)
5'-UNI: 5'-GGCCACGCGTCGACTAGTACG (SEQ ID NO: 19)

IWF5 3' RACE.

The amino acid sequence of the IWF5 protein was used to construct two degenerated oligonucleotide primers for the isolation of a partial cDNA clone by 3'RACE. Total RNA was purified from sugar beet (cv. Monova) leaves 6 days after inoculation with *C. bericola* according to Collinge et al. 1987 (Plant Mol. Biol 8: 405–414). Reverse transcription followed by PCR was done with the RT-PCR kit from Perkin Elmer and according to their protocol. Briefly, 1 μg of total RNA and 2.5 pmol $Q_T$-primer was incubated at 42° C. for 45 min with reverse transcriptase followed by incubations at 99° C. for 5 min and 5° C. for 5 min. In the first PCR 40 pmol of the primer $Q_0$ was used as downstream primer and the upstream primer was 150 pmol of the degenerated primer (5'-GC(ACGT)TG(CT)(AC)G(ACGT)TG(CT) ATGAA: position 315–331 in the IWF5 cDNA sequence (SEQ ID NO: 20)). In the second nested PCR 50 pmol of the primer $Q_1$ was used as downstream primer and the upstream primer was 50 pmol of the degenerated primer (5'-GG (ACGT)AT(ACT)AA(CT)CA(CT)AA(GA)TA: position 354–370 in the IWF5 cDNA sequence (SEQ ID NO: 21)). The PCR conditions were: 1 min at 94° C., 2 min at 42° C., 1 min at 50° C. and 5 min at 72° C. for 1 cycle followed by 1 min at 94° C. and 2 min at 42° C. and 3 min at 72° C. for 35 cycles followed by 10 min at 72° C. After the second PCR a single DNA product of 390 bp was obtained. The DNA product was cloned into the pT7Blue vector (Novagen) and sequenced using a Termo Sequenase fluorescent cycle sequencing kit (Amersham) and an ALF DNA sequencer (Pharmacia).

IWF5 5'RACE.

The sequence of the 5' end of IWF5 cDNA was obtained by 5'RACE using the 5'RACE system from Gibco BRL with 3 gene specific primers constructed from the partial cDNA sequence obtained by 3'RACE. Briefly, 1 µg of the same total RNA as used for 3'RACE and 2.5 pmol of a gene specific primer GSP5-1 (5'-TGGAATTGG-AGATTATGTAAG: position 619–643 in the IWF5 cDNA sequence (SEQ ID NO: 22)) was incubated at 70° C. for 10 min followed by the addition of reverse transcriptase and incubating at 42° C. for 30 min, 70° C. for 15 min and the addition of RNaseH and incubating further 10 min at 55° C. The cDNA was dC-tailed according to the protocol of Gibco BRL. The tailed cDNA was subjected to two rounds of PCR. In the first PCR 20 pmol of the 5'-ANKER primer was used as upstream primer and the downstream primer was 20 pmol of the gene specific primer GSP5-2 (5'-TCACTTTAGATGTAAGAAGCACA-CATG: position 596–622 in the IWF5 cDNA sequence (SEQ ID NO: 23)). In the second PCR 50 pmol of the 5'-UNI primer was used as upstream primer and the downstream primer was 50 pmol of the gene specific primer GSP5-3 (5'-TAAGCAGAAAGTTCCAGAAAGCA-TG: position 548–572 in the IWF5 cDNA sequence (SEQ ID NO: 24)). The condition for the first PCR was: 1 min at 94° C. and 1 min at 51° C. and 2 min at 72° C. for 35 cycles followed by 10 min at 72° C. The condition for the second PCR was: 1 min at 94° C. and 1 min at 55° C. and 2 min at 72° C. for 35 cycles followed by 10 min at 72° C. The single 600 bp DNA product was cloned into the pT7Blue vector (Novagen) and sequenced using a Termo Sequenase fluorescent cycle sequencing kit (Amersham) and an ALF DNA sequencer (Pharmacia).

IWF6 3' RACE.

The amino acid sequence of the IWF6 protein was used to construct two degenerated oligonucleotide primers for the isolation of a partial cDNA clone by 3'RACE. Total RNA was purified from sugar beet (cv. Monova) leaves 6 days after inoculation with *C. beticola* according to Collinge et al. 1987 (Plant Mol. Biol 8: 405–414). Reverse transcription followed by PCR was done with the RT-PCR kit from Perkin Elmer and according to their protocol. Briefly, 1 µg of total RNA and 2.5 pmol $Q_T$-primer was incubated at 42° C. for 45 min with reverse transcriptase followed by incubations at 99° C. for 5 min and 5° C. for 5 min. In the first PCR 40 pmol of the primer $Q_0$ was used as downstream primer and the upstream primer was 150 pmol of the degenerated primer (5'-GG(AGCT)TA(CT)TG(CT)AA(CT)AT(ACT)(TC)T: position 297–313 in the IWF6 cDNA sequence (SEQ ID NO: 25)). In the second nested PCR 50 pmol of the primer $Q_1$ was used as downstream primer and the upstream primer was 50 pmol of the degenerated primer (5'-AA(CT)GT(ACGT)TG(CT)TG(CT)GC(ACGT)GG: position 314–332 in the IWF6 CDNA sequence (SEQ ID NO: 26)). The PCR conditions were: 1 min at 94° C., 2 min at 42° C., 1 min at 50° C. and 3 min at 72° C. for 1 cycle followed by 1 min at 94° C. and 2 min at 42° C. and 3 min at 72° C. for 35 cycles followed by 10 min at 72° C. After the second PCR a single DNA product of 320 bp was obtained. The DNA product was cloned into the pT7Blue vector (Novagen) and sequenced using a Termo Sequenase fluorescent cycle sequencing kit (Amersham) and an ALF DNA sequencer (Pharmacia).

IWF6 5' RACE.

The sequence of the 5' end of IWF6 cDNA was obtained by 5'RACE using the 5'RACE system from Gibco BRL with 3 gene specific primers constructed from the partial cDNA sequence obtained by 3'RACE. Briefly, 1 µg of the same total RNA as used for 3'RACE and 2.5 pmol of a gene specific primer GSPF1 (5'-CATCAAGA-AGTCCATAATTGTCTAG: position 508–532 in the IWF6 CDNA sequence (SEQ ID NO: 27)) was incubated at 70° C. for 10 min followed by the addition of reverse transcriptase and incubating at 42° C. for 30 min, 70° C. for 15 min and the addition of RNaseH and incubating further 10 min at 55° C. The cDNA was dC-tailed according to the protocol of Gibco BRL. The tailed cDNA was subjected to two rounds of PCR. In the first PCR 20 pmol of the 5'-ANKER primer was used as upstream primer and the downstream primer was 20 pmol of the gene specific primer GSP6-2 (5'-TGATCTTTATTGAC-AAACAGACGC: position 473–498 in the IWF6 CDNA sequence (SEQ ID NO: 28)). In the second PCR 50 pmol of the 5'-UNI primer was used as upstream primer and the downnstream primer was 50 pmol of the gene specific primer GSP6-3 (5'-ACAGACACGCTAGTT-AGATGACTAAGC: position 456–482 in the IWF6 CDNA sequence (SEQ ID NO: 29)). The condition for the first PCR was: 1 min at 94° C. and 1 min at 51° C. and 2 min at 72° C. for 35 cycles followed by 10 min at 72° C. The condition for the second PCR was: 1 min at 94° C. and 1 min at 55° C. and 2 min at 72° C. for 35 cycles followed by 10 min at 72° C. The single 510 bp DNA product was cloned into the pT7Blue vector (Novagen) and sequenced using a Termo Sequenase fluorescent cycle sequencing kit (Amersham) and an ALF DNA sequencer (Pharmacia).

IWF7 3' RACE.

The amino acid sequence of the IWF7 protein was used to construct two degenerated oligonucleotide primers for the isolation of a partial cDNA clone by 3'RACE. Total RNA was purified from sugar beet (cv. Monova) leaves 6 days after inoculation with *C. beticola* according to Collinge et al. 1987 (Plant Mol. Biol 8: 405–414). Reverse transcription followed by PCR was done with the RT-PCR kit from Perkin Elmer and according to their protocol. Briefly, 1 µg of total RNA and 2.5 pmol $Q_T$-primer was incubated at 42° C. for 45 min with reverse transcriptase followed by incubations at 99° C. for 5 min and 5° C. for 5 min. In the first PCR 40 pmol of the primer $Q_0$ was used as downstream primer and the upstream primer was 150 pmol of the degenerated primer (5'-GA(AG)CA(AG)AA(AG)CC(ACGT)TGA(CT)(CT)T: position 247–263 in the IWF7 cDNA sequence (SEQ ID NO: 30)). In the second nested PCR 50 pmol of the primer $Q_1$ was used as downstream primer and the upstream primer was 50 pmol of the degenerated primer (5'-TG(CT)GG(ACGT)TA(CT)TA(CT)AA(AG)AA: position 265–286 in the IWF7 cDNA sequence (SEQ ID NO: 31)). The PCR conditions were: 1 min at 94° C., 2 min at 42° C., 1 min at 50° C. and 3 min at 72° C. for 1 cycle followed by 1 min at 94° C. and 2 min at 42° C. and 3 min at 72° C. for 35 cycles followed by 10 min at 72° C. After the second PCR a single DNA product of 270 bp was obtained. The DNA product was cloned into the pT7Blue vector (Novagen) and sequenced using a Termo Sequenase fluorescent cycle sequencing kit (Amersham) and an ALF DNA sequencer (Pharmacia).

IWF7 5' RACE.

The sequence of the 5' end of IWF7 cDNA was obtained by 5'RACE using the 5'RACE system from Gibco BRL with 3 gene specific primers constructed from the partial cDNA sequence obtained by 3'RACE. Briefly, 1 µg of the same total RNA as used for 3'RACE and 2.5 pmol of a gene specific primer GSP7-1 (5'-CCTAATTTC-CCTCAAATCACG: position 443–463 in the IWF7 CDNA sequence (SEQ ID NO: 32)) was incubated at 70° C. for 10 min followed by the addition of reverse transcriptase and incubating at 42° C. for 30 min, 70° C. for 15 min and the addition of RNaseH and incubating further 10 min at 55° C.

The cDNA was dC-tailed according to the protocol of Gibco BRL. The tailed cDNA was subjected to two rounds of PCR. In the first PCR 20 pmol of the 5'-ANKEK primer was used as upstream primer and the downstream primer was 20 pmol of the gene specific primer GSP7-2 (5'-AATTTCCCTCAAATCACGAATTGAG: position 436–460 in the IWF7 cDNA sequence (SEQ ID NO: 33)). In the second PCR 50 pmol of the 5'-UNI primer was used as upstream primer and the downstream primer was 50 pmol of the gene specific primer GSP7-3 (5'-TCGTCAGTTGGCTCATTTTGGG: position 400–423 in the IWF7 cDNA sequence (SEQ ID NO: 34)). The condition for the first PCR was: 1 min at 94° C. and 1 min at 5 1° C. and 2 min at 72° C. for 35 cycles followed by 10 min at 72° C. The condition for the second PCR was: 1 min at 94° C. and 1 min at 55° C. and 2 min at 72° C. for 35 cycles followed by 10 min at 72° C. The single 450 bp DNA product was cloned into the pT7Blue vector (Novagen) and sequenced using a Termo Sequenase fluorescent cycle sequencing kit (Amersham) and an ALF DNA sequencer (Pharmacia).

Production of Transformed Plants

The genes encoding proteins according to the invention are introduced into plants. Based on gene specific primers, the coding regions of the genes encoding the proteins are synthesized from corresponding mRNA using PCR. After addition of promoter and terminator sequences, the genes encoding the said proteins are introduced into a plant transformation vector. The vector may optionally include a gene encoding a WIN protein, such as that obtained from stressed barley leaf or barley grain, and/or a gene encoding one or more of the proteins depicted in SEQ ID Nos. 4 to 9. and/or a gene encoding a chitinase and or a glucanase. One possible chitinase is the chitinase 4 described in PCT Patent Application No. PCT/DK92/00108 (Publication No. WO 92/17591). *Agrobacterium tumefaciens*, for example, may be transformed with these vectors. Plant cells are then treated with such transformed Agrobacterium. and the thus transformed plant cells are regenerated into whole plants, in which the new nuclear material is stably incorporated into the genome. It will be appreciated, however, that the DNA encoding a protein according to the present invention, (or combination of such proteins), optionally further encoding other proteins, may be introduced into plant cells by other known methods, including use of a micro-projectile gun, electroporation, electro-transformation, and micro-injection etc, and that regeneration of transformed plant cells is carried out according to methods known to the skilled man, including treatment of the cells with cytokines where this is necessary or desirable in order to improve the regeneration frequency.

Moreover, suitable microorganisms (i.e. those in which the production of the present inventive proteins is not substantially toxic) may be transformed with a vector comprising the gene (or genes) encoding the protein so that the transformed micro-organisms produce such protein. The micro-organisms may further comprise the genes encoding other proteins, such as a WIN protein and/or a protein the sequence of which is depicted in one or more of SEQ ID Nos. 4–9. Furthermore, such other proteins may further comprise various chitinases and/or glucanases. One possible such other protein is the chitinase 4 as described in PCT Patent Application No. PCT/DK92/00108 (Publication No. WO 92/17591).

These micro-organisms may then be used to combat plant pathogens. For example the transformed micro-organisms may be dried and sprayed onto infected plants or plants at risk of infection.

What is claimed is:

1. An isolated protein having anti-fungal activity against Cercospora spp., said protein comprising an amino acid sequence having at least 95% sequence identity to a sequence selected from the group consisting of: SEQ ID NO:3 wherein the amino acid in position 80 is alanine instead of valine, SEQ ID NO:5, and SEQ ID NO:6.

2. The protein according to claim 1, said protein comprising the amino acid sequence depicted in SEQ ID NO:3 wherein the amino acid in position 80 is alanine instead of valine, SEQ ID NO:5, or SEQ ID NO:6.

3. An anti-fungal composition having activity against Cercospora spp., said composition comprising the protein according to claim 1.

4. A process for inhibiting growth of fungi of Cercospora spp., comprising exposing said fungi to the protein according to claim 1 in an amount sufficient to inhibit growth of said fungi.

5. A process for isolating the protein according to claim 1 comprising macerating a material containing said protein, wherein said material is *Beta vulgaris* or a transformed microorganism or plant expressing said protein and subjecting said macerated material to solvent extraction to thereby isolate said protein.

6. The protein according to claim 1, said protein comprising the amino acid sequence having at least 95% sequence identity to SEQ ID NO:3 wherein the amino acid in position 80 is alanine instead of valine.

7. The protein according to claim 1, said protein comprising the amino acid sequence having at least 95% sequence identity to SEQ ID NO:5.

8. The protein according to claim 1, said protein comprising the amino acid sequence baying at least 95% sequence identity to SEQ ID NO:6.

9. The protein according to claim 2 comprising SEQ ID NO:3 wherein the amino acid in position 80 is alanine instead of valine.

10. The protein according to claim 2 comprising SEQ ID NO:5.

11. The protein according to claim 2 comprising SEQ ID NO:6.

* * * * *